United States Patent [19]

Beer

[11] Patent Number: 5,663,491

[45] Date of Patent: Sep. 2, 1997

[54] METHOD FOR STEAM QUALITY MEASUREMENT

[75] Inventor: Gary L. Beer, Plano, Tex.

[73] Assignee: Atlantic Richfield Company, Los Angeles, Calif.

[21] Appl. No.: 951,640

[22] Filed: Sep. 25, 1992

[51] Int. Cl.$^6$ .................................................. G01N 25/60
[52] U.S. Cl. ........................... 73/61.41; 73/29.03; 374/42
[58] Field of Search .............................. 73/29.01, 29.03, 73/30.02, 61.41; 374/42

[56] References Cited

U.S. PATENT DOCUMENTS

| | | | |
|---|---|---|---|
| 4,193,290 | 3/1980 | Sustek, Jr. et al. | 73/29 |
| 4,681,466 | 7/1987 | Chien et al. | 73/861.04 |

OTHER PUBLICATIONS

"Steam Quality and Metering", T. M. Wilson, The Journal of Canadian Petroleum Technology, Apr.–Jun. 1976.

"Kern River Field Test of a Steam Quality Measurement Technique", C.L. Redus, et al, SPE Paper No. 17445, Society of Petroleum Engineers, 1988.

*Primary Examiner*—Timothy McMahon
*Attorney, Agent, or Firm*—Michael E. Martin

[57] ABSTRACT

Steam quality in flow lines equipped with orifice meters may be determined by injecting a predetermined quantity of water into the flow line and measuring the orifice pressure differential with and without water injection. An approximation of the James correlation, which relates the orifice differential pressure, the total fluid mass flow rate and steam quality raised to the 1.5 power, may be used for conditions both before and during water injection together with an energy balance for conditions both before and during water injection to determine steam quality before water injection. A portable water injection unit may be temporarily connected to each flow line at a tap installed in the flow line upstream of the orifice. The effect of water injection for each flow condition may be prior confirmed by injecting a predetermined quantity of water downstream of the orifice based on an initial estimate of dry steam flow in the line.

5 Claims, 1 Drawing Sheet

METHOD FOR STEAM QUALITY MEASUREMENT

BACKGROUND OF THE INVENTION

1. Field of the Invention

The present invention pertains to a method of measuring steam quality, particularly in flow lines to heavy oil production wells and the like, using a sharp-edged orifice and injection of a measured quantity of water into the flowstream passing through the orifice.

2. Background

So-called heavy oil production from subterranean reservoirs often involves the use of steam to stimulate movement of the viscous oil into the production wells. The steam is typically supplied to individual injection wells through a network of distribution pipes or "lines" from a central steam generation facility such as an electric cogeneration plant. Accordingly, the steam quality may vary somewhat in the complex distribution system and the individual supply lines leading to the respective injection wells.

Various techniques have been proposed for measuring the quality of the steam flow to each of the injection wells. Control over steam quality is important to balance the amount of energy being injected into a particular formation in order to control oil production and the efficiency of the stimulation process. Techniques which have been developed for measuring steam quality include, for example, that disclosed in U.S. Pat. No. 4,193,290 to Sustek, Jr., et al which describes an acoustic transducer associated with an orifice. Publications entitled "Kern River Field Test of a Steam Quality Measurement Technique" by C. L. Redus, et al (Society of Petroleum Engineers Publication No. SPE 17445, 1988) and "Steam Quality and Metering" by Thomas M. Wilson, The Journal of Canadian Petroleum Technology, April–June, 1976 also discuss methods for measuring steam quality utilizing a sharp-edged orifice or so-called orifice meter.

One objective in improving methods for measuring steam quality is to utilize existing facilities, where possible. Many steam distribution systems for stimulating the production of heavy oil include, in the individual, relatively small-diameter steam flow lines to each well, an existing sharp-edged orifice together with means for measuring the pressure drop across such an orifice. With these existing systems in mind, it has been determined that it would be desirable to develop a relatively uncomplicated and inexpensive method and system for surveying relatively small-diameter steam flow lines to measure steam quality in these lines from time to time and utilize such information for better control of the stimulation of the particular heavy oil reservoir.

The system and method described in the Sustek, Jr. patent requires the use of an acoustic transducer and an installation of an orifice whose acoustic signature is known from previous tests. Moreover, the technique described in the SPE publication requires installation of an orifice plate in series with a critical flow choke in each of the lines. This technique would require retrofitting of a substantial number of existing lines which incorporate only an orifice plate. Still further, the method described in the above-referenced article in the Journal of Canadian Petroleum Technology requires the use of flow meters, again, a technique which requires installation of flow meters and nozzles into already existing facilities. The disadvantages of these approaches are thus significant in existing, large and complex steam distribution networks. However, the method of the present invention substantially overcomes the disadvantages of prior art methods and systems.

SUMMARY OF THE INVENTION

The present invention provides a unique method for measuring steam quality, particularly in relatively small diameter flow lines which include sharp-edge orifice plates or similar orifice meters which determine fluid flow by measuring a pressure drop thereacross. The present invention, in particular, provides an improved a method for determining steam quality in the individual distribution lines of a steam distribution network for stimulating the production of heavy oil from subterranean reservoirs.

In accordance with one important aspect of the present invention a method for measuring steam quality in a flow line is provided wherein a correlation between steam quality, a pressure drop across an orifice, and the mass flow of fluid through the orifice is used for two flow conditions. In particular, the use of an approximation of a mathematical correlation developed by R. James ("Metering of Steam-Water Two-Phase Flow by Sharp Edged Orifices", Proc. Inst. Mech. Engrs., Vol. 180, No. 23, pp. 549–566 (1965)) together with the injection of a measured quantity of water into the steam flow line and the measurement of the pressure drop across the existing orifice plate, both with and without the measured water injection, is utilized to determine steam quality.

The method of the present invention also provides for determining the quality of steam flow utilizing an approximation of the James correlation for two measured pressure differentials across an orifice, one with a measured quantity of water injection and one without the introduction of a measured quantity of water into the flow line, together with the calculation of an energy balance from known conditions of steam temperature, injected water temperature, specific heat of injected water and the latent heat of vaporization of steam. Accordingly, the quality of steam flowing through a flow line may be determined by measurements taken both before and after injection of a known quantity of water upstream of an orifice plate, utilizing the James correlation and an energy balance equation, whereby plural equations may be solved simultaneously to determine the steam quality.

In accordance with the method of the present invention, steam distribution lines which include existing orifice meters may be measured to determine the quality of steam flow by introduction of a relatively small amount of water using equipment which is portable and inexpensive and does not require interruption of steam flow through the line being tested. Moreover, existing steam flow lines may be easily modified by merely adding small branch conduits or "taps" to the lines upstream and downstream of the existing orifice plate without disassembly of the line or without interrupting the steam flow within the line.

Those skilled in the art will further appreciate the advantages and superior features of the invention together with other important aspects thereof upon reading the detailed description which follows in conjunction with the drawing.

DESCRIPTION OF PREFERRED EMBODIMENTS

Figure 1:
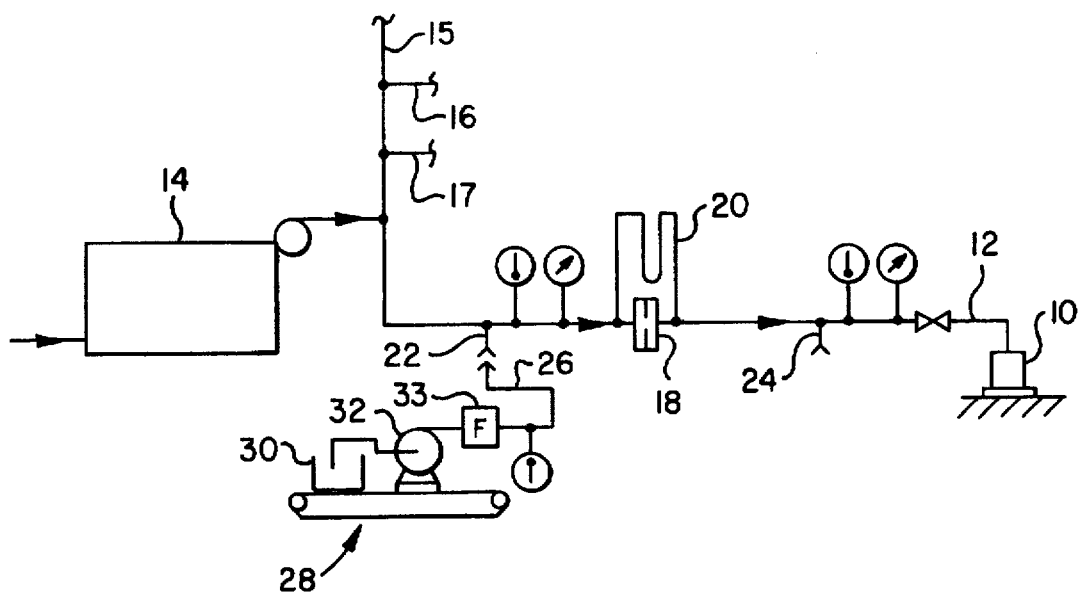
FIG. 1 is a schematic diagram of a portion of a steam distribution network for injecting steam into subterranean wells and showing the components used in the method of the present invention.

In the drawing, FIG. 1 is a schematic diagram in which conventional components are shown in schematic or diagrammatic form and in certain ones of the equations unit conversion constants may be omitted, all in the interest of clarity and conciseness.

Referring to FIG. 1, there is illustrated an exemplary arrangement according to the present invention for injecting steam into a steam injection well for stimulating the production of heavy oil from a subterranean reservoir. The injection well is indicated by the numeral 10 and is connected to a steam injection flow line or conduit 12 which, in turn, is operably connected to a source of steam such as a generator 14. The generator 14 may also distribute steam to a network which includes other flow lines 15, 16 and 17 leading to similar injection wells, not shown. Each of the relatively small-diameter steam injection lines or conduits 12, 15, 16 and 17 are adapted to include a conventional sharp-edged orifice plate 18, one shown for the line 12, interposed therein, together with suitable means 20 for measuring a fluid pressure differential across the orifice plate. The pressure differential measurement means 20 may comprise a conventional manometer or pressure differential gauge of any suitable configuration.

In accordance with the present invention, the individual flow lines, such as the flow line 12, leading to injection wells are modified to include small branch conduits 22 and 24 which may be connected to the flow line using conventional "hot tapping" procedures upstream and downstream of the orifice plate 18, respectively. The locations of the branch conduits or taps 22 and 24 may each be a linear distance on the order of 50 to 100 times the nominal diameter of the conduit 12 from the position of the orifice plate 18, respectively.

The schematic diagram of FIG. 1 indicates that pressure and temperature measurements may be taken between the tap 22 and the orifice plate 18 in the conduit 12 and between the tap 24 and the well 10, respectively. These pressure and temperature measurements may be obtained by conventional pressure and temperature measuring means. Moreover, the taps or branch conduits 22 and 24 may also be fitted with quick disconnect couplings for connection to a water supply conduit 26 which is part of a water supply unit generally designated by the numeral 28. The water supply unit 28 may include a source of water of known temperature and suitable purity such as a tank 30 which is in communication with a pump 32 operably connected to the conduit 26. The pump 32 is capable of delivering a measured amount or flow rate of water through the conduit 26 into the conduit 12 by way of either one of the branch conduits or taps 22 or 24. The temperature of the water being injected into the conduit 12 from the unit 28 may also be measured as indicated in the diagram of FIG. 1. The amount or flow rate of water injected into the conduit 12 may be determined from a suitable flow measuring device 33 or by a known displacement of the pump 32.

One important advantage of the method of the present invention is that only one pump and flow meter unit 28 is required to test any number of flow lines since the unit may be moved from line to line and connected to each line at branch conduits or taps upstream and downstream of the orifice plate disposed in each line. As will be understood from the following description it may, in many instances, not be necessary to install the unit 28 for operation at the downstream tap, such as the tap 24 in FIG. 1. However, to improve the accuracy of the measurement technique, it is considered desirable to test the conditions in the steam flow line, in each case, by pumping water into the line at the downstream connection or tap 24 before the method is carried out to determine steam quality.

The instant method utilizes the above-mentioned correlation established by James which may be approximated by the use of certain equations to be described below. The method according to the present invention for determining quality of steam flow in the conduit 12, for example, uses an approximation of the James correlation which is as follows:

$$H = W(W/K)X^{1.5} \qquad (a)$$

Wherein

H = the orifice pressure reading taken, for example, from the pressure differential gauge means 20 in inches of water, W = the steam flow in pounds per hour, K = the saturation temperature of steam at the measured pressure conditions upstream of the orifice plate 18 in °F., and X = the steam quality.

Steam quality is defined as the ratio of steam flow to total mass flow. An estimation of the flow rate of steam is made assuming the flow is dry steam (X=1). The saturation temperature (K) at the pressure and temperature conditions upstream of the orifice 18 is obtained from steam tables (Keenan, Keyes, et al, "Steam Tables", 1969). Accordingly, an estimate of dry steam flow may be obtained from equation (a).

The unit 28 is then connected at the downstream tap 24 and a measured quantity-or flow rate of water is injected into the conduit 12 at about one-half or somewhat less of the flow rate of the above-mentioned estimate of dry steam flow. After a suitable period of time to reach steady-state conditions (about 10 minutes) the orifice differential pressure is noted at the gauge means 20. If the pressure differential reading does not vary by more than about five percent (5%) from the previous reading at the assumed dry steam conditions, then the original pressure differential reading is used for the further calculations in accordance with the method of the invention. If the pressure differential reading with water injection at downstream tap 24 changes by more than about five percent (5%) then the pressure differential value read with the downstream injection is used for further calculations in accordance with the method of the invention.

After testing the influence, or lack thereof, of the water injection at the downstream tap 24, the unit 28 is moved to connect its discharge line 26 to the upstream tap 22. Water is then injected into the conduit 12 at the above-mentioned rate for a like period of time to achieve steady-state conditions and an orifice differential reading is taken from the gauge means 20 which now reflects the effect of the water flow. The orifice pressure differential reading, together with pressure and temperature readings of the fluid flow in conduit 12 upstream of the orifice 18 and a reading of the temperature of the injection water is then used in a series of calculations as set forth hereinbelow. The calculations assume that a constant pressure mixing process occurs with little heat loss in the conduit 12. Steam quality may be determined from the following set of equations wherein equations (b) and (c) are approximations of the James correlation from equation (a), for the respective conditions noted.

$$H_1 = W_1(W_1/K)X_1^{1.5} \qquad (b)$$

Wherein $H_1$ is the orifice differential reading prior to injection of water into the tap 22, $W_1$ is the mass flow rate in pounds per hour prior to injection of water into the conduit 12, K is the saturation temperature of steam at the conditions in the conduit 12 upstream of the orifice 18, and X is the steam quality.

$$H_2 = W_2(W_2/K)X_2^{1.5} \qquad (c)$$

Equation (c) is for the conditions with water injection into the line 12.

$$W_2 = W_1 + Y \qquad (d)$$

wherein Y is the water injection rate in pounds per hour.

Moreover, an energy balance may be computed from the following equation:

$$Z = W_1 X_1 - W_2 X_2 \qquad (e)$$

wherein Z is the amount of steam which condenses to raise the injected water to the fluid flow temperature in line 12. This quantity may be computed from the following equation:

$$Z = c_p(T_s - T_y)Y/\lambda_s \qquad (f)$$

Wherein $c_p$ equals the specific heat or "heat capacity" of water, which is taken at the temperature and pressure of the flow in the conduit 12 upstream of the orifice 18, $T_s$ is the steam temperature upstream of the orifice 18 prior to water injection, $T_y$ is the temperature of the injected water, Y is the injection water flow rate in pounds per hour and $\lambda_s$ is the latent heat of vaporization of steam at the pressure in the conduit 12 upstream of the orifice 18 prior to water injection, which may be determined from steam tables.

Accordingly, the amount of steam which condenses (Z) may be determined based on the water injection conditions from equation (f) and substituted in Equation (e).

The above set of equations (b) through (e) represent four equations and four unknowns, the unknowns being the steam quality under the initial conditions and during water injection ($X_1$, $X_2$), respectively, and the total fluid mass flow rates under both conditions ($W_1$, $W_2$). The steam quality and mass flow rate under one condition can be expressed in terms of the steam quality and mass flow rate under the other condition and Equation (b) may be solved for the steam quality, $X_1$. The computations may, of course, be carried out by machine processes including the computation to determine Z.

From the foregoing, it will be appreciated that a relatively uncomplicated procedure may be carried out for determining the quality of steam flow in lines containing orifice meters wherein the quality measurement may be taken over a relatively short period of time without interrupting steam flow to the end use such as a steam injection well, without adversely affecting the steam flow to the end use during the measurement period and without the use of expensive equipment or processes which comprise permanent installations in each of the lines. The unit 28 may be, as mentioned previously, be moved from one steam flow line to another to carry out the measurement process and the steam flow through each line may then be adjusted to balance the energy being input to a particular reservoir based on the quality of steam flow. The size of the unit 28 may require a pump capacity no greater than about 10 gallons per minute and the pump connection taps 22 and 24 may be relatively small diameter, one-half inch nominal pipe size, for example, and may be installed in steam flow lines without interrupting steam flow using conventional "hot tapping" techniques for installing branch conduits in flow lines operating under flow conditions.

Figure 2:
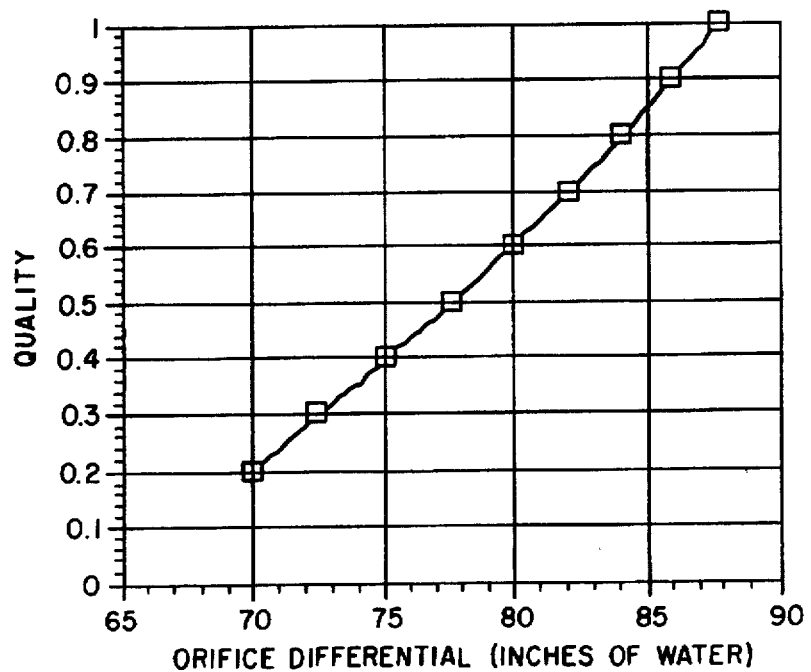
FIG. 2 is a diagram showing the correlation between steam quality and measurements of orifice differential pressure in a line-conducting two-phase steam-water flow for a particular operating condition.

Referring briefly to FIG. 2, there is illustrated a diagram which confirms the efficacy of the method of the invention wherein steam quality versus the orifice differential pressure, in inches of water, is plotted for a typical field condition wherein the initial differential pressure across the orifice 18 was assumed to be 100 inches of water, the steam rate was 424 barrels (42 gallons) per standard day of cold water equivalent and the water injection rate was carried out at a rate of 200 barrels per standard day. Nominal steam pressure in the line 12 under the measurement conditions was assumed to be 400 psig.

Although a preferred embodiment of the present invention has been described in detail herein, those skilled in the art will recognize that certain substitutions and modifications may be made to the method without departing from the scope and spirit of the invention recited in the appended claims.

What is claimed is:

1. A method for determining the quality of steam flowing in a section of a steam flow line, said section of flow line having a single orifice interposed therein, said method comprising the steps of:

measuring the temperature of fluid in said section of flow line upstream of said single orifice;

measuring the pressure differential across said single orifice due to steam flow through said single orifice;

injecting water into said section of flow line upstream of said single orifice;

measuring the rate of injection of said water;

measuring the temperature of said water in said section of flow line before injection of said water into said section of flow line;

measuring the pressure differential across said single orifice during injection of said water into said section of flow line; and determining the quality of said steam flowing in said section of flow line from said measurements of the pressure differentials across said single orifice prior to injecting water into said section of flow line and during injection of water into said section of flow line and the amount of steam which is condensed to raise the temperature of said water prior to injection of water into said section of flow line to the temperature of fluid flow in said section of flow line during water injection into said section of flow line, and wherein said amount of steam condensed is determined from the steam temperature in said section of flow line prior to injection of water into said section of flow line, the temperature of said injected water, the heat capacity of said water, the latent heat of vaporization of steam at the pressure in said section of flow line upstream of said single orifice prior to injection of water into said section of flow line and said flow rate of water injected into said section of flow line.

2. The method set forth in claim 1 wherein:

the amount of steam condensed (Z) is determined from the equation:

$$Z = c_p(T_s - T_y)/\lambda_s$$

wherein $c_p$ equals the specific heat of water, which is taken at the temperature and pressure of the flow in said section of flow line upstream of said single orifice, $T_s$ is the steam temperature upstream of said single orifice, $T_y$ is the temperature of the injected water, Y is the injection water flow rate and $\lambda_s$ is the latent heat of vaporization of steam at the pressure in said section of flow line upstream of said single orifice.

3. The method set forth in claim 2 wherein:

steam quality is determined from a correlation between the parameters of pressure differential across said single orifice, the mass flow rate of fluid through said section of flow line and the saturation temperature of steam based on equations $$H_1 = W_1(W_1/K)X_1^{1.5} \tag{b}$$

wherein $H_1$ is the pressure differential across said single orifice prior to injection of water into said section of flow line, $W_1$ is the mass flow rate prior to injection of water into said section of flow line, K is the saturation temperature of steam in said section of flow line upstream of said single orifice, and $X_1$ is the steam quality, $$H_2 = W_2(W_2/K)X_2^{1.5} \tag{c}$$

wherein equation (c) is for said parameters at the conditions with water injection into said section of flow line, $$W_2 = W_1 + Y \tag{d}$$

wherein Y is the water injection rate, and $$Z = W_1 X_1 - W_2 X_2 \tag{e}$$

4. The method set forth in claim 1 including the step of:

determining an estimated mass flow rate of steam flow in said flow line based on the measurements of temperature in said section of flow line upstream of said single orifice and the pressure differential across said single orifice prior to water injection into said section of flow line and assuming that said steam flow is dry steam flow.

5. The method set forth in claim 4 wherein:

the step of injecting water is carried out by injecting water at a mass flow rate which is about one half the estimated mass flow rate of dry steam flow.

* * * * *